United States Patent [19]

Jones et al.

[11] Patent Number: 4,915,691
[45] Date of Patent: Apr. 10, 1990

[54] ASPIRATOR

[75] Inventors: Charles A. Jones; George E. Sinko, both of San Antonio, Tex.

[73] Assignee: Gesco International, Inc., San Antonio, Tex.

[21] Appl. No.: 235,720

[22] Filed: Aug. 22, 1988

Related U.S. Application Data

[63] Continuation of Ser. No. 47,727, May 7, 1987, abandoned.

[51] Int. Cl.⁴ .............................................. A61M 1/66
[52] U.S. Cl. ...................................... 604/73; 604/319; 604/321; 604/406; 604/902
[58] Field of Search .................. 604/30, 35, 317, 319, 604/321, 320, 406, 902, 73

[56] References Cited

U.S. PATENT DOCUMENTS 1,889,425  11/1932  Sorensen ................................ 604/35
4,257,425  3/1981   Ryan ..................................... 604/319
4,273,126  6/1981   Grane et al. .......................... 604/319

FOREIGN PATENT DOCUMENTS 3500538  7/1986  Fed. Rep. of Germany ...... 604/319
1019560  2/1966  United Kingdom .................. 604/35

Primary Examiner—C. Fred Rosenbaum
Assistant Examiner—Kathleen A. Daley
Attorney, Agent, or Firm—Cox & Smith Incorporated

[57] ABSTRACT

A self-contained hand held medical aspirating device having a piston-grip type handle for holding in one hand with a standard connector for connecting to a catheter and a vacuum line for connecting to a vacuum source and a removable specimen container for receiving body fluids and a fluid barrier means to prevent body fluids from getting into the suction source.

15 Claims, 2 Drawing Sheets

ASPIRATOR

This application is a continuation of co-pending application Ser. No. 047,727, filed on May 7, 1987 now abandoned.

BACKGROUND OF THE INVENTION

The invention relates to a medical suction apparatus, and in particular to a medical suctioning device for the aspiration of mucus, amniotic fluids, meconium stained fluids, and meconium plugs from naso-oropharyngyl passages, the stomach and the trachea (wide pipe) of newborn infants, as well as other body fluids from any patient. The device utilizes mechanically generated negative pressures that can be regulated accurately by the clinician with a thumb control designed in the apparatus.

The invention also relates to a means for collecting samples of aspirants while at the same time providing it with the capability for intermittent ventilation of the patient when involved with the respiratory system. All of the above features are incorporated into an all inclusive device that can be held and operated with one hand.

Suctioning, or the aspiration of body fluids in medical surgico-clinical procedures, is a critical, but necessary, routine occurrence and over the years there have been a myriad of ways that suction has been accomplished. From a practical point of view, these diverse means for suctioning have been reduced to a few methods that are currently utilized on a daily basis. These rather antiquated methods of suctioning have generally been thought adequate in the past, but with the advent of new viral diseases, such as AIDS, that are transmitted through body fluids, a serious concern over the safety of such conventional methods has arisen. The current method for aspiration leaves the physicians and clinicians vulnerable to infection by these infectious diseases due to the intimate contact necessary to accomplish this procedure which, in most cases, includes oral suctioning of the body fluid.

In the case of a newborn infant, the aspiration or suctioning procedure is extremely critical during the first few minutes of a newborn's life and begins when the infant's head emerges, even before delivery of the body and before breathing begins. Studies have shown that the inhalation of amniotic fluid by the infant, particularly with meconium stained fluids, can cause respiratory distress syndrome, a common cause of infant mortality. In the delivery room, when aspirating for a meconium plug, it is a common clinical practice to insert an endotrachial tube (catheter) below the infant's larynx (vocal cords) and apply suction to the tube directly with the physician's mouth. Although a surgical mask or sterile gauze is usually interspersed between the mouth and the end of the tube (catheter), a recent study indicated that 74% of the physicians reporting had ingested secretions during oral meconium suctioning. Bacteria and viruses are readily aerosolized and/or atomized, hence the present method for suctioning potentially exposes the clinicians to AIDS, chlamydia, gonorrhea, hepatitis, herpes, and syphilis.

Manifesting the problem to a greater degree, U.S. Pat. No. 3,610,242 describes a commonly used device for the aspiration of the oropharnyx, nasopharynx, and the stomach. However, as depicted in FIG. 8 of this patent, negative pressure is induced and controlled by the clinician with his or her mouth, exposing them to body fluids. This patent clearly demonstrates that commonly used technique which is no longer acceptable for this day and age.

Most of the diverse tools that are currently utilized for suctioning body fluids in conjunction with mechanically produced vacuum (wall suction) use a thumb control or a finger tip control as an add on to the plumbing, necessitating the use of both hands. One hand is generally necessary to regulate the amount of suction being delivered and the other hand is usually used to manipulate the direction and placement of the catheter within the patient. This type of procedure is shown in FIG. 1 of U.S. Pat. No. 3,610,242 mentioned above. Using both hands makes it difficult, if not impossible, for the clinician to hold an illuminated laryngoscope or a light source to better view his or her work or to position and restrain the patient during catheter placement or, in fact, the actual suctioning process itself. As is apparent, such techniques necessitate more than two hands to be properly accomplished. Another type of apparatus manifesting similar inadequacies is shown in U.S. Pat. No. 4,334,538 and includes a handle 11 with a finger control vacuum regulating hole 18. However, the device disclosed in that patent is limited by the disadvantage that it can be used only for obtaining very small samples of fluid from within the ear or other areas which are very difficult to access.

Furthermore, should airway suctioning be required (an din the newborn, the majority of the suctioning has to do with the respiratory system), the introduction of a vacuum into the respiratory tract withdraws needed oxygen from the patient's lungs causing the patient to turn blue. Removal of oxygen in this manner necessitates the removal of the suction cathether and the reintubation of the patient with another catheter having an appropriate adaptor for proper connection to standard ventilating equipment.

An object of the invention is to provide to the medical-surgical setting an all inclusive aspirating (suctioning) device for the removal of body fluids. In particular, for newborn infants, the device provides for the suctioning of amnionic fluids, meconium stained fluids, and mucus from the mouth, oropharynx, nasopharynx, and stomach as well as meconium plugs from the tracheas (air ways) of term and premature infants in a safe and efficacious manner for all parties in the procedure. Another object of the present invention is to provide a suctioning device or aspirator that can be held and operated with one hand; can utilize mechanical or wall-type vacuum, eliminating the need for oral suctioning; can accurately vary the amount of suction through a catheter by means of a conveniently located thumb control port; can be fitted with an easily removable fluid trap for collecting samples needed for testing; can be appropriately baffled internally to to direct all aspirants into the fluid trap, can incorporate a filter within the baffles to prevent fluids from getting into the vacuum source, hence, confining possible infecting contaminants; can be easily adapted for the utilization of different types, sizes, and lengths of catheters affording quick connections and disconnections; can be adapted to provide intermittent patient ventilation with standard, readily available equipment; can afford the physician the ability to use the catheter separately when involved with delicate intubations, after which the body of the suctioning device can be quickly reconnected; can be of a configuration so as to afford a clear and unobstructed view during the intubation or the suctioning process; can be constructed of materials, packaged, and furnished sterile at a low enough cost for one time use, thereby eliminating the possibility of cross contamination or re-infection by the insidious viruses known today; and can be manipulated quickly and easily in situation in which time could affect a life. the invention has been described in conjunction with the foregoing specific embodiment, many alternatives, variations and modifications will be apparent to those of ordinary skill in the art and those alternatives, variations and modifications are intended to fall within the spirit and scope of the appended claims.

SUMMARY OF THE INVENTION

A hand held medical aspirating apparatus is provided with a body member that has a pistol grip-like shape to conveniently fit and be held and operated in one hand of a clinician. A standard respiratory connector means is provided on the body member for receiving a catheter for suctioning body fluid. A tubular means is provided for connecting the apparatus with a source of vacuum such as the wall vacuum or portable mechanical means for providing of negative pressures in hospitals. A removable vial or container is inserted into the body member and is connected thereto with a screw thread connector so that it may be sealed but readily removed. In order to insure that the body fluid which is drawn up through a catheter goes into the vial or container, a baffle system with an internal fluid barrier is provided to deflect the body fluid into the vial or container and to prevent the body fluid from being drawn into the vacuum system.

DETAILED DESCRIPTION OF PREFERRED EMBODIMENT

Figure 1:
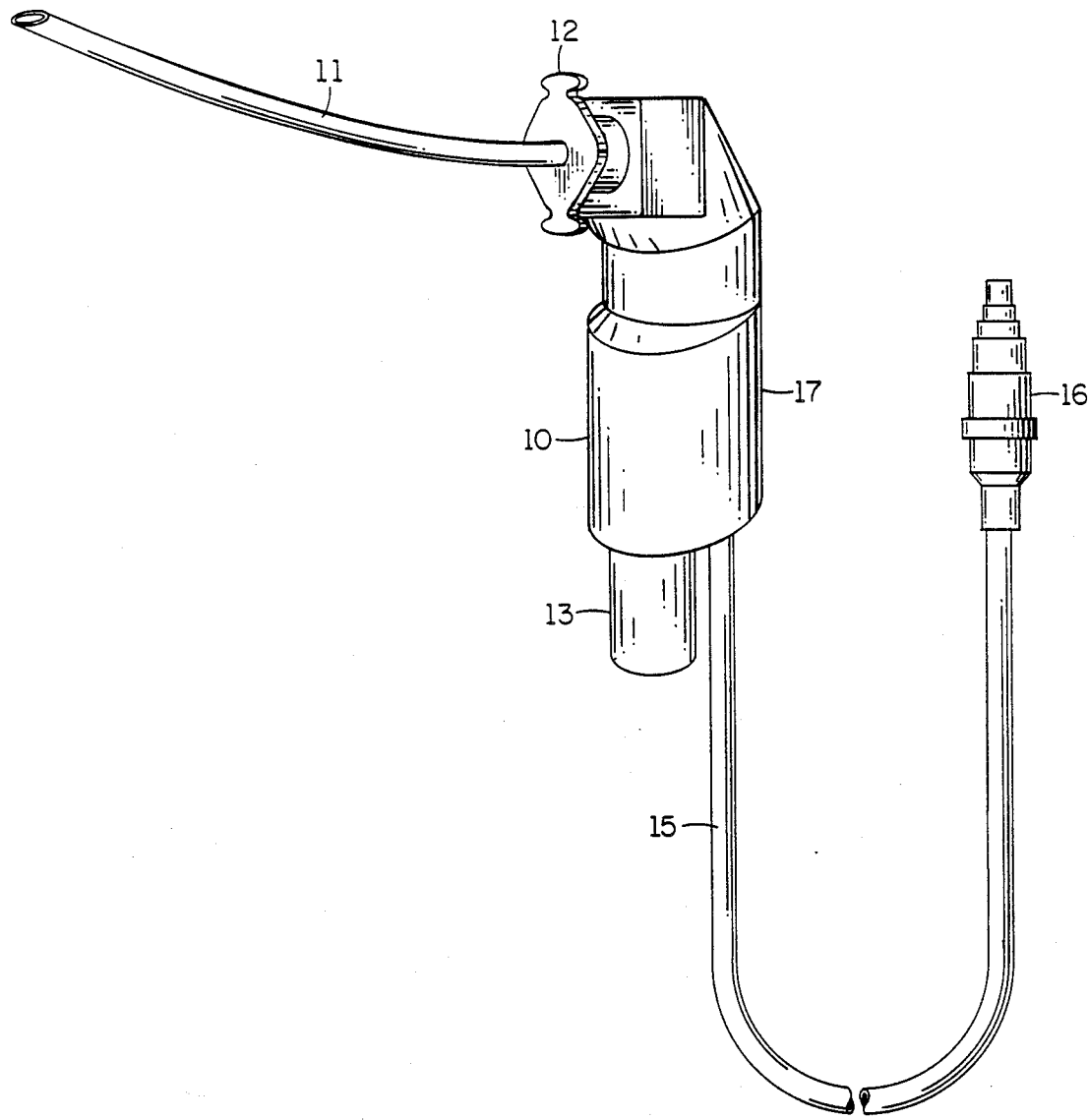
FIG. 1 is a perspective view of the aspirator of the invention.
Figure 2:
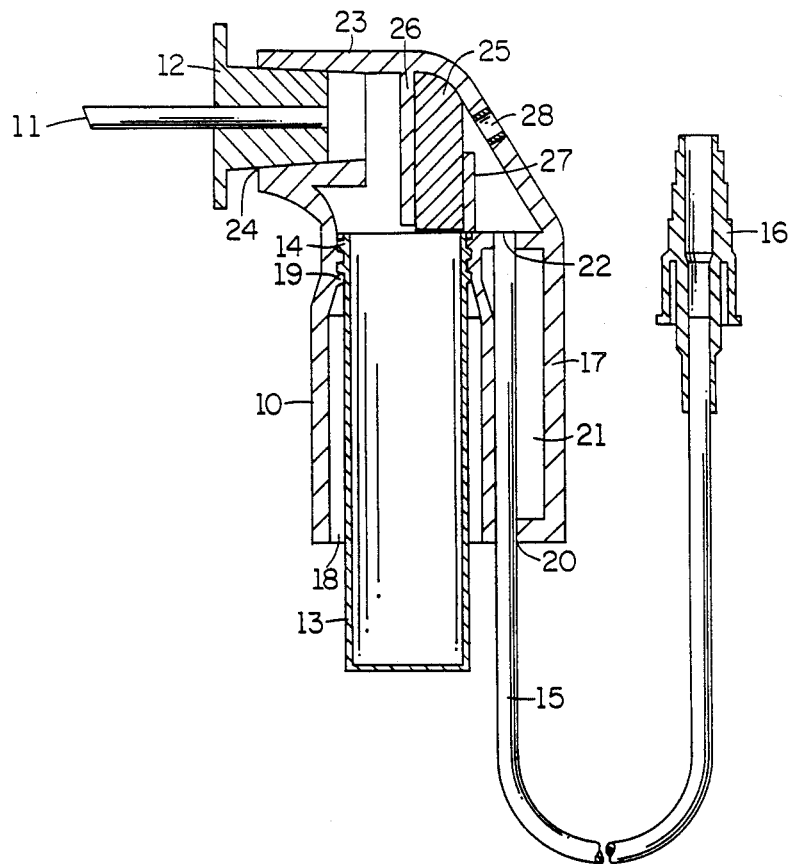
FIG. 2 is a sectional view of the apparatus of FIG. 1 taken along the lines 2—2 in FIG. 1
Figure 3:
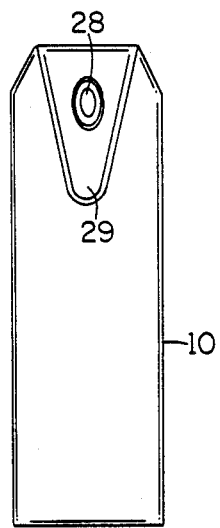
FIG. 3 is a vertical plan view of the body portion from the back showing the thumb control.

The aspirator 10 includes a catheter 11 having a standard connector 12 on the end thereof. Vial or container 13 has screw type threads 14 for releasable connection to the body portion 17. Vacuum supply tube 15, having a standard connector 16 mounted on the end thereof, is connected to a vacuum source (not shown).

The body portion 17 is generally elliptical in a cross-section and is designed to be held in and fit in one's hand. The interior portion of body portion 17 includes a cylindrical opening 18 at the bottom of the cavity in body portion 17 which receives a vial or container 13. Screw threads 19 at the upper portion of the interior cylindrical portion of body protion 17 connect with the screw threads 14 of the vial or container 13 to removably hold vial or container 13 in place on body portion 17.

A tube 15 is inserted through opening 20 and extends upwardly through the cylindrical opening 21. An opening or hole 22 is provided at the upper portion of the cylindrical portion 21 for communicating vacuum from the source with the interior cavities of the body portion 17.

The upper portion 23 of the aspirator 10 includes a cylindrical opening 24 into the cavity with body portion 17 which receives the standard adapter 12. A baffle 26 extends all the way across the upper portion 23 of body portion 17, partially closing the cavity therethrough, so that any fluids entering the cavity therein through the catheter 11 are directed against the baffle and downwardly into the vial or specimen container 13. Another baffle 27 helps prevent fluids from going through the opening 22 into the vacuum tube or line 15. At the back of the aspirator 10 is a thumb hole 28 located on concave surface 29 at the back of the body portion 17. A liquid fluid barrier or filter 25 can be inserted between baffles 26 and 27 to prevent fluids and other matter from being drawn into the vacuum source. The filter 26 may be comprised of a sponge-like material that is compressible which can inserted into and will conform to the space between the baffles 26 and 27. When filter 25 is comprised of such materials and is contacted by liquid, the sponge-like material tends to block the passage of liquid.

In operation, the device shown in FIG. 1 is held in the user's hand with the thumb positioned adjacent the thumb control hole 28. The vacuum line 15 is attached to a vacuum source. When the thumb hole 28 is opened to the atmosphere, the vacuum source draws air through the thumb hole 28 through the opening 22 and out through the line 15. When it is desired to utilize the device, the catheter 11 is positioned adjacent the area to which suction is to be applied and one merely partially or wholly closes off the thumb hole 28 by applying one's thumb. Application of the thumb results in suction being applied to the catheter 11. When fluids enter the catheter 11, they are directed toward the baffle system and impinge on baffle 26 so that they are necessarily directed downwardly into the specimen container or vial 13. The thumb hole control 28 may be partially closed off with one's thumb or fully closed off to vary the amount of suction that is applied through the catheter 11. This control allows one to apply a large amount of suction when necessary or a small amount when that is all that is required. The baffle 27, along with the fluid barrier 25, which forms part of the baffle system, also extends from one side of the body portion 17 to the other side and prevents the fluids in the specimen container from migrating into the opening 22.

As is apparent, the invention allows use of the device with a single hand, freeing up the other hand of the physician to position the patient. The catheter 11 may merely be directed to the area to which suction is to be applied and with the pistol grip like body portion 17 the suction easily can be directed and applied with only one hand.

Universal tubing adapter 16 permits use of the device with standard vacuum tubing typically used in hospitals with motorized suction. The specimen container vial 13 may be easily removed by unscrewing the threads 14 from the threads 19 and they may be replaced with another vial 13 when desired. The device is made up of typical plastic materials suitable for medical use.

The body portion 17 of the aspirator 10 should be in the shape of a pistol-grip handle for easy handling. The short length of tubing 15 extending from the bottom of the body portion or pistol grip handle 17 is integral with of the body portion 17 to facilitate connecting aspirator 10 to mechanical or wall-type suction with the universal type step adapter 16, thereby separating the clinician from intimate contact with the patient and a patient's body fluids. The specific design and shape of the body portion 17 permits a clinician to accurately control the amount of suction being delivered to the patient by means of the thumb control port or hole 28 conveniently located near the top radius of the pistol-grip handle where the thumb would normally be positioned when held in user's hand. The body portion 17 may be molded from plastic, since it is hollow, with the internal threads 19. The hollow portion easily accepts a cylindrical collection vial or container at a similar thread 14 on the neck so that it can be screwed into the hollow body in sealing relationship to receive the suctioned body fluids. After the body fluids have been collected, the vial 13 can be easily unscrewed, removed from the hollow handle, and after sealing the vial with a sealing lid or top via the screw threads 14, the body fluids sent to the laboratory for testing. The internal cylindrical opening 24 of the pistol-grip handle may be sized to accept a standard 15 mm respiratory adapter. Catheters having a male 15 mm adapter can be connected and disconnected at will using the standard friction fitting. This structure also permits the use of a variety of cathether lengths and diameters depending upon the situation confronting the clinician. The opening of connector 12 is designed and situated to maintain the internal dimension of the lumen of catheter 11 in use throughout its entire length to eliminate any restriction to the flow. The connector 12, which fits into the connecting opening 24 of the pistol grip-like handle or body portion 17, will also accept female adapters of any standard ventilating system for any intermittent ventilation of the patient, when needed, without the need of reintubation of the patient. The configuration of the pistol-like handle 17 is such that the major componentry fits well within the hand of the operator, thereby providing a clear and unobstructed view of the patient area being suctioned. The invention may be typically made of high impact thermoplastic material which can be molded in two halves and then joined together with ultra-sonic welding or solvent bonding so as to achieve a tight seal.

The pistol grip design makes the invention easy to use with one hand, freeing the other hand for holding the light source such as a laryngoscope or for positioning and restraining movement of the patient. The thumb control 28 is designed to be conveniently located to facilitate accurate control over the amount of suction and eliminating the need for oral suctioning when mechanical or wall type suctioning is available. It is, of course, understood that oral suctioning could be provided, when mechanical means are not available, through the connector 16 when the thumb control hole is blocked.

The internally baffled airway system is designed into the invention to direct the body fluids into the integral but removable vial or specimen container 13 to reduce or eliminate fluids reaching the vacuum source. In emergencies where a vacuum source is not available, these internal baffles 26 and 27 facilitate the use of the aspirator 10 with oral suction, but still afford the clinician more protection than equipment currently in sue.

The fluid barrier or filter 25, hydrophobic in nature, prevents fluids from being drawn through the orifice 22 into the suction system and contaminating it.

The use of male and female adapters with standard dimension allows for easy change in catheter sizes and affords easy adaptability to ventilating equipment, thereby permitting intermittent ventilation of the patient as required. Furthermore, the adapter design is such that the inner lumen of the catheters involved is not restricted.

Inasmuch as a typical suctioning procedure requires entrance into delicate areas of the body, intubation can be a critical step. However, since catheters can be connected and handled individually, the physician can introduce the catheter by itself and once in place re-connect the body portion 7 of the aspirator 10 and proceed with suctioning as necessary.

The removable vial or specimen container 13 acts as a fluid trap and the threaded neck 14 allows vial 13 to be easily sealed and unscrewed from the pistol grip handle 17. This ease of removal permits body fluids to be captured and then transported to laboratories for culture and analysis. For simple adaptation to standard vacuum tubing used in the hospitals with motorized mechanical suctioning equipment, a universal type tubing adapter 16 (Christmas tree type adapter), is fitted onto the end of vacuum line 15. Because of the general configuration of the aspirator 10, along with the versatility and ease with which connections and disconnections can be made for the utilization of different types and sizes of catheters, the device easily adapts to the individual techniques of the clinicians involved and eliminates the long learning curve generally associated with the utilization of a new piece of equipment.

Although the invention has been described in conjunction with the foregoing specific embodiments, many alternatives, variations and modifications will be apparent to those of ordinary skill in the art who have the benefit of its disclosure. Those alternatives, variations and modifications are intended to fall within the spirit and scope of the following appended claims.

We claim:

1. A handheld medical aspirating apparatus comprising:
    a body member having a pistol grip-like shape for holding in one hand and a cavity therethrough;
    means forming one opening of the cavity in said body member for receiving a standard catheter connector therein for suctioning liquid from the body of a patient;
    means forming a second opening of the cavity in said body member for connecting the body member to a vacuum source;
    a vacuum control means positioned at the upper portion of the body member for engagement by the thumb when said body member is held in the hand of the user;
    removable vial means sealingly connected to the bottom of said body member for receiving and collecting liquid from the body of a patient; and
    means for deflecting liquid pulled into the cavity in said body member by the vacuum source downwardly into the vial and for preventing liquid from being drawn into said vacuum source connecting means when said body member is held in a generally upright position.

2. The apparatus as set forth in claim 1 wherein said means for preventing liquid from being drawn into said vacuum source connecting means comprises a barrier.

3. The apparatus as set forth in claim 2 additionally comprising a second barrier, said first and second barriers comprising a baffle system for preventing migration of liquid into the vacuum source.

4. The apparatus as set forth in claim 3 wherein said filter comprises a sponge-like or fibrous material positioned between said first and second barriers.

5. The apparatus as set forth in claim 1 wherein said body member is elliptical in cross-section.

6. The apparatus as set forth in claim 1 wherein said body member is formed of high impact thermoplastic material.

7. The apparatus as set forth in claim 1 wherein said vacuum control means comprises an opening in said body member communicating with the passage therethrough that can be selectively closed off with the thumb of the user.

8. A handheld aspirator comprising:
a body member having a cavity therethrough and a pistol grip-like shape for holding in one hand;
means forming one opening of the cavity in said body member for receiving a standard catheter connector therein;
means forming a second opening of the cavity in said body member for connecting the interior of the cavity in said body member to a vacuum source:
means forming a third opening of the cavity in said body member for engagement by the thumb of the hand in which said body member is held for controlling the vacuum;
a vial releasably mounted to the bottom of said body member, the interior of said vial communicating with the cavity in said body member, for receiving liquid from a patient when the cavity in said body member is connected to a vacuum source;
a barrier integrally formed in said body member and extending across a portion of the cavity therethrough for deflecting liquid pulled into the cavity downwardly into said vial when the cavity is connected to a vacuum source; and
means for preventing liquid from being drawn into said vacuum source connecting means when said body member is in a generally upright position.

9. The apparatus as set forth in claim 8 wherein said third opening means is positioned on a concave surface of said body member.

10. A handheld aspirator comprising:
a body member having a cavity therethrough and a pistol grip-like shape for fitting within one hand of an operator;
means in the wall of said body member forming one opening of the cavity in said body member for receiving one end of a first tube for connecting the interior of the cavity to the body of a patient to suction liquid from the area adjacent to the other end of the first tube;
means in the wall of said body member forming a second opening of the cavity is said body member for receiving one end of a second tube, the other end of the second tube being connected to a vacuum source, for connecting the interior of the cavity to a vacuum source;
means in the wall of the upper portion of said body member forming a third opening of the cavity in said body member, thereby connecting the cavity in said body member with the atmosphere, for selective engagement with the thumb of the hand of the operator to control the amount of suction applied to the area adjacent to the end of the first tube;
a vial releasably mounted to the bottom of said body member, the interior of said vial communicating with the cavity in said body member, for receiving liquid from a patient when the second tube is connected to a vacuum source;
a barrier in the cavity in said body member for deflecting liquid drawn into the cavity away from said second opening means when the second tube is connected to a vacuum source and said body member is connected thereto; and
a filter for preventing deflected liquid from being drawn through said second opening means into the vacuum source.

11. The apparatus as set forth in claim 10 wherein said third opening means is positioned on a concave surface of said body member.

12. The apparatus as set forth in claim 10 wherein said barrier comprises a baffle system.

13. The apparatus as set forth in claim 12 wherein said baffle system comprises first and second barriers extending across a portion of the cavity in said body member.

14. The apparatus as set forth in claim 10 wherein said filter is positioned between said first and second barriers.

15. The apparatus as set forth in claim 10 wherein said first opening means comprises means for receiving a standard cathether connecter therein.

* * * * *